United States Patent [19]

Brewer

[11] Patent Number: 5,762,877
[45] Date of Patent: Jun. 9, 1998

[54] CHEMICAL SAMPLE CONCENTRATING DEVICE

[76] Inventor: William E. Brewer, 26 Cedarfield Ct., Columbia, S.C. 29212

[21] Appl. No.: 733,496

[22] Filed: Oct. 18, 1996

[51] Int. Cl.⁶ ........................................ B01L 3/02
[52] U.S. Cl. .................. 422/100; 73/61.54; 73/61.55; 73/61.59; 210/198.3; 422/70; 422/101; 436/162; 436/177; 436/180
[58] Field of Search ................ 422/100, 70, 101; 436/177, 180, 162, 161; 210/198.2, 198.3; 73/61.54, 61.55, 61.59

[56] References Cited

U.S. PATENT DOCUMENTS

| | | |
|---|---|---|
| 3,523,890 | 8/1970 | Stahl . |
| 3,738,493 | 6/1973 | Cumming et al. ............... 210/198.3 |
| 3,757,952 | 9/1973 | Baitsholts et al. . |
| 3,766,884 | 10/1973 | Rosenthal . |
| 3,807,959 | 4/1974 | Russell et al. . |
| 3,843,053 | 10/1974 | Thoden . |
| 3,857,784 | 12/1974 | Martinez . |
| 3,895,758 | 7/1975 | Thoden . |
| 3,988,921 | 11/1976 | Lightner . |
| 4,263,144 | 4/1981 | Platt . |
| 4,696,187 | 9/1987 | Kopp et al. . |
| 4,843,243 | 6/1989 | Biemann et al. . |
| 5,591,644 | 1/1997 | Karmen ............................ 436/53 |

*Primary Examiner*—Jan Ludlow
*Attorney, Agent, or Firm*—Michael A. Mann

[57] ABSTRACT

The present invention advances a chemical concentrating device for use with thin layer chromatographic, gas chromatographic, high pressure liquid chromatographic, and capillary electrophoresis analysis. The concentrating device has a T-shaped member having a first and second annular branch in axial alignment and a third branch perpendicular to the first and second branches. When used in thin layer chromatographic analysis, the T-shaped member is placed over the syringe needle with the end of the needle extending below the second branch. A gas source in fluid communication with the third branch forwards gas in an annular pattern about the end of the needle, thereby evaporating the solvent within the sample and confining the sample to a particular geometrical area on the thin layer chromatography plate. When used with other chromatographic techniques, the T-shaped member is removably affixed to a syringe needle having a beveled end. The introduction of an annular gas flow about the beveled end evaporates the solvent and concentrates the sample at the needle's end.

13 Claims, 6 Drawing Sheets

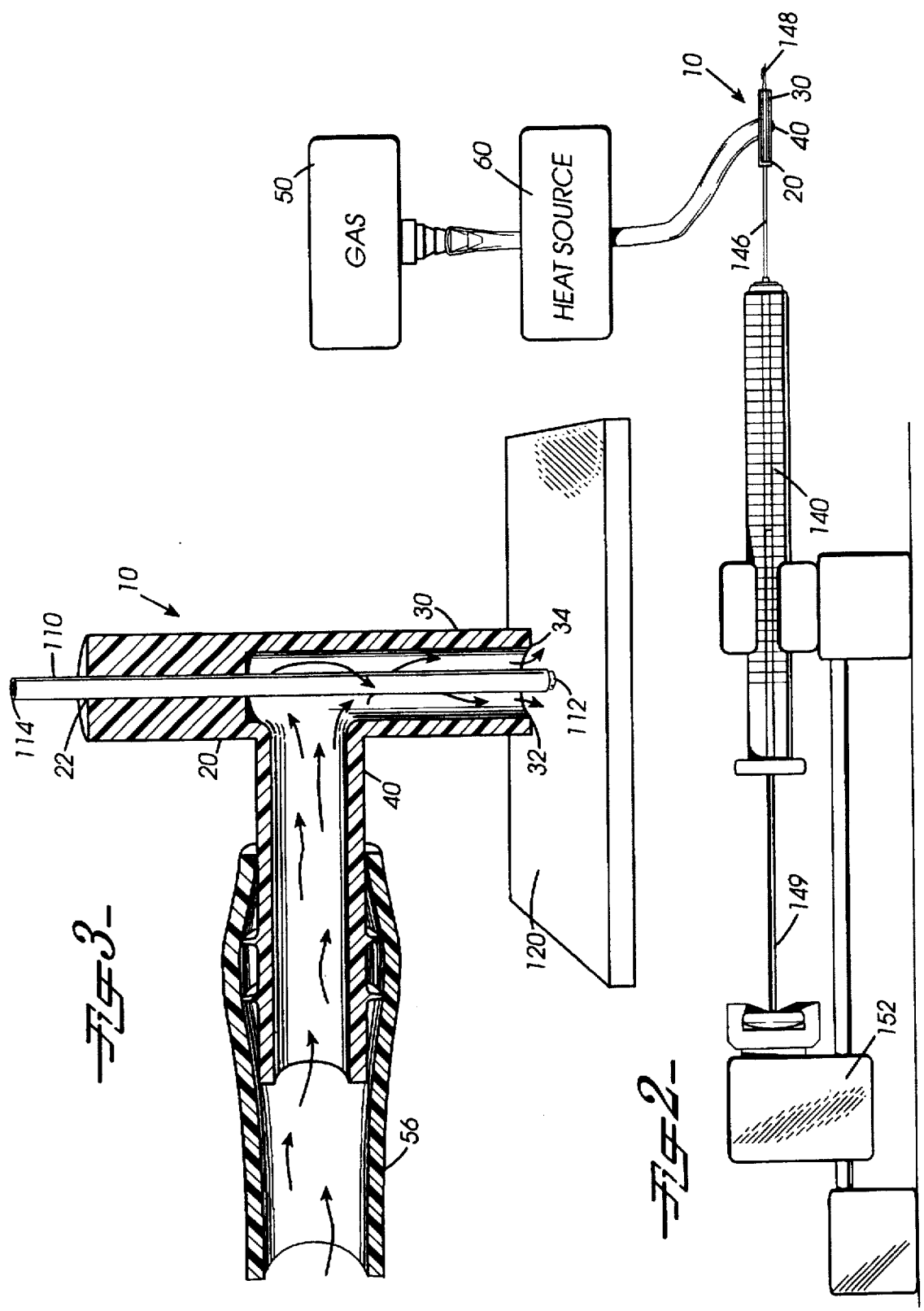

CHEMICAL SAMPLE CONCENTRATING DEVICE

BACKGROUND OF THE INVENTION

1. Field of the Invention

The present invention relates to devices used to prepare chromatographic samples. In particular, the present invention is a chemical concentrating device for use in preparing samples for thin layer and gas chromatography.

2. Discussion of Background

Thin layer chromatography, commonly referred to as TLC, is a widely used chemical separation and detection technique, especially in the areas of medicinal chemistry, organic and inorganic synthetic chemistry, and toxicology. The process involves placing a chemical sample approximately 1.0 cm from the end of a plate of absorbent material such as silica gel, cellulosic material, or alumina. Once the sample is deposited on the surface of the plate, it is dried to remove any solvents. After the sample is dried, the end of the plate which is proximate to the deposited sample is placed within an organic solvent having a depth of approximately 0.5 cm. The solvent travels up the plate through capillary action and causes the migration of the analyte along the plate. Each particular chemical compound within the sample will migrate at a different rate and therefore will be deposited in different positions along the TLC plate. Once full migration has occurred, the plate is dried and compared to a reference chromatogram to identify the particular chemical species present within the sample.

One problem confronted with the use of TLC is premature migration of the sample immediately subsequent to its deposition on the TLC plate. If the sample is not completely dried and maintained within a well defined geometrical area, the sample will migrate. This premature migration often results in the improper identification of chemical species during the analysis of the chromatogram. In addition, only 1–2 μL of sample is usually deposited on the plate, since a small "spot" is required to ensure proper separation of the analytes. Therefore, this method of analysis often lacks adequate sensitivity and is normally used only for chemical samples with high concentrations of analyte.

Another well known technique in the field of analytical chemistry is gas chromatography. In gas chromatography, a sample is dissolved in an organic solvent and injected into a heated inlet port. The sample is immediately vaporized and transported, by the use of a carrier gas, into a chromatography column having absorbent material packed therein. As the chemical compounds exit the chromatography column, they are detected and registered on a recorder. The compounds having a greater affinity for the absorbent material will exit the chromatography column at a slower rate than those with less affinity.

One problem experienced in the use of gas chromatography, as well as high pressure liquid chromatography (HPLC), capillary electrophoresis, and other similar methods of analysis, is the inability of the detector to detect trace amounts (less than 1.0 ppm) of certain chemical compounds. This lack of sensitivity is most often due to an insufficient concentration of analyte that is introduced to the chromatographic method. In the case of gas chromatography, only 1.0 to 3.0 μL of sample is typically injected for analysis. As an example, if the gas chromatography vial contains 100 μL of solution and only 2 μL are injected, then 98% of the sample goes undetected. This problem is significant since many areas of science, such as toxicology and environmental chemistry, routinely require the analysis of trace amounts of analyte.

Therefore, there exists a need for a chemical concentrating device that adequately overcomes the problems existing in preparing chemical samples for chromatographic separation techniques.

SUMMARY OF THE INVENTION

According to its major aspects and broadly stated, the present invention is a device and method for concentrating chemical samples on a thin layer chromatography plate and for concentrating a chemical sample prior to its introduction to a gas chromatograph, high pressure liquid chromatograph, capillary electrophoresis, or similar analytical instruments. The device comprises a T-shaped member having a first and second annular branch in axial alignment and a third annular branch perpendicular to the first and second branches. The first branch is formed with an inner diameter which is slightly larger than the outer diameter of a syringe needle used in chromatographic techniques, thereby allowing frictional engagement between the syringe and the T-shaped connector. The third branch of the member is in fluid communication with a source of gas.

In a preferred embodiment of the present invention used to prepare a sample for thin layer chromatographic analysis, a syringe containing a needle having a flat end is inserted into the first branch of the T-shaped member and pushed therethrough until the end of the needle is a preselected distance below the end of the second branch. The end of the needle is then lowered over the thin layer chromatographic plate until contact is made between the end of the needle and the surface of the plate. Thereafter, the gas source is activated to send gas at a preselected flow rate into the T-shaped member. The gas travels through the T-shaped member and is expelled through the second branch in an annular pattern around the end of the needle. As the sample is being injected into the plate, the flow of gas about the outer diameter of the needle evaporates the solvent contained within the sample and concentrates the analyte within a geometrical area defined by the outer diameter of the needle end.

In an alternative preferred embodiment of the present invention used to prepare a sample for injection into a gas chromatograph, high pressure liquid chromatograph or a capillary electrophoresis instrument, a syringe containing a needle having a beveled end is inserted into the T-shaped member with the beveled end extending a preselected distance beyond the end of the second branch. The gas source is then activated to provide gas flow about the beveled end of the needle. A force is then exerted on the syringe plunger to forward the sample to the beveled end. The flow of gas about the beveled end causes the evaporation of the solvent within the sample and leaves concentrated analyte at the needle's end. When a predetermined volume of the analyte/solvent mixture remains within the syringe, the flow of gas is terminated and the concentrated sample is injected into the chromatographic instrument for analysis.

In both preferred embodiments, it is preferred that the gas be heated to a temperature between approximately 40° C. to 60° C. prior to introducing the gas into the T-shaped member. The method by which the gas is heated can be any method normally employed in the art of analytical chemistry. The T-shaped member can be manufactured from any material commonly used in the art and can be sized to fit any size syringe needle.

A very important feature of the present invention is the use of an annular branch fitted about the perimeter of the syringe needle, which enables the expulsion of gas in an annular pattern about the end of the needle. When used in thin layer chromatography, the application of gas in an annular flow pattern ensures efficient evaporation of the solvent contained within the sample deposited on the plate. Moreover, by providing an annular flow pattern about the outer diameter of the needle, the deposited sample is confined within a small, uniform, well-defined geometrical area. This in turn prevents the migration of the sample and thus permits greater accuracy in the identification of chemical species present within the sample. In addition, the annular flow pattern about the outer diameter of the needle enables all of the sample (not just 1.0 to 3.0 µL of sample) to be applied to the thin layer chromatography plate.

When used to prepare a sample for introduction to a gas chromatograph, high pressure liquid chromatograph, or a capillary electrophoresis instrument, the use of an annular gas flow pattern allows the evaporation of the solvent and the deposition of a concentrated chemical sample at the tip of the syringe needle. This concentrated sample at the end of the needle enables the introduction of 100% of the analyte into the chromatographic or electrophoresis instrument. As a result, the sensitivity of the resulting analysis is increased significantly and often enables the detection of species which were heretofore undetectable.

Other features and advantages of the present invention will be apparent to those skilled in the art from a careful reading of the Detailed Description of a Preferred Embodiment accompanied by the following drawings.

BRIEF DESCRIPTION OF THE DRAWINGS

In the drawings,

FIG. 2 is a front view of a chemical concentrator according to a preferred embodiment of the present invention;

FIG. 3 is a detailed cross-sectional view of a chemical concentrator according to an alternative preferred embodiment of the present invention;

DETAILED DESCRIPTION OF A PREFERRED EMBODIMENT

The present invention is a chemical sample concentrating apparatus and a method for concentrating a sample. The present invention can be used in conjunction with thin layer chromatography, gas chromatography, high pressure liquid chromatography, and capillary electrophoresis to concentrate a chemical sample for analysis.

Figure 1:
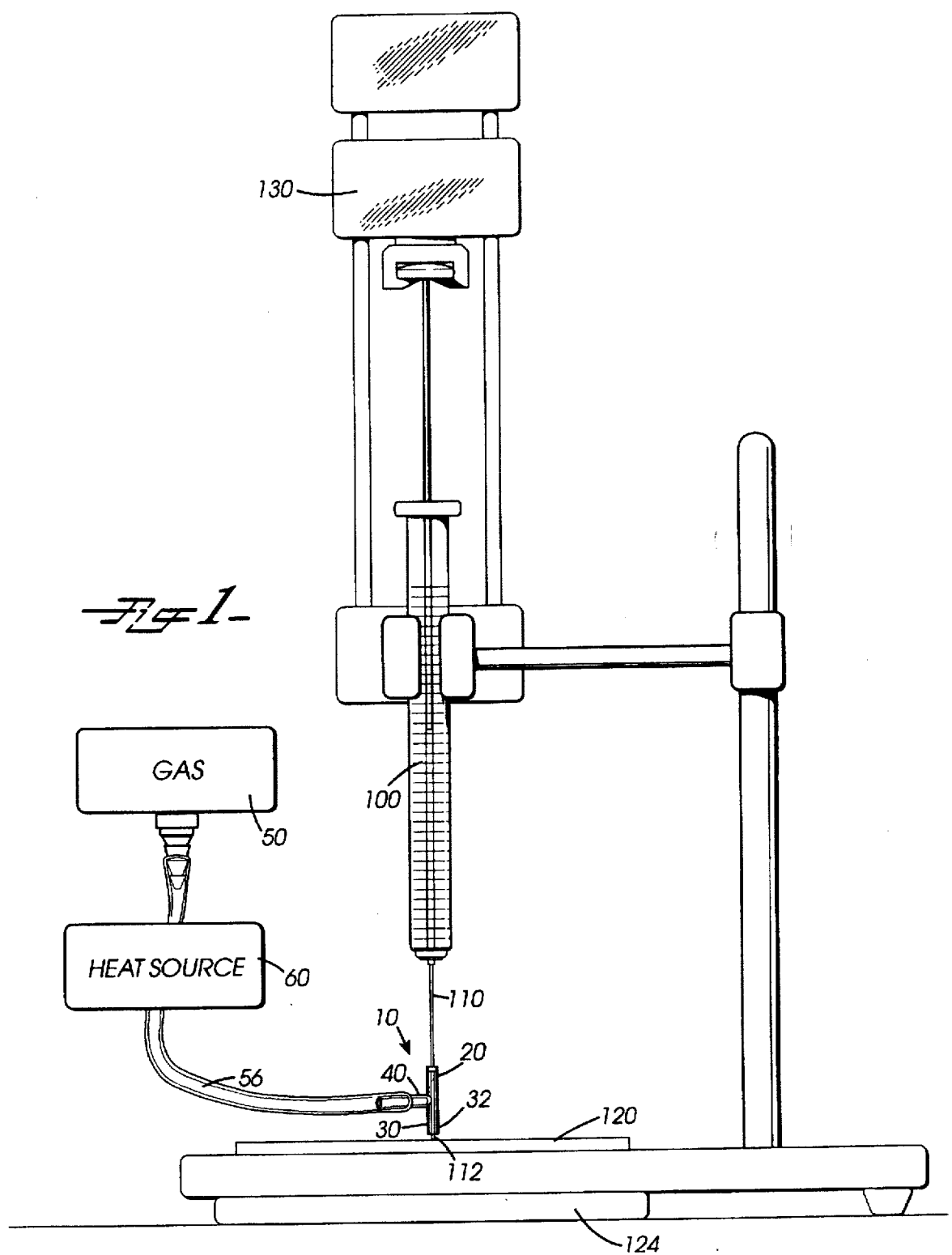
FIG. 1 is a partial cross-sectional front view of a chemical concentrator according to a preferred embodiment of the present invention, illustrated in use with a thin layer chromatographic plate.

Referring now to FIGS. 1 and 3, there is shown a front view and a detailed cross-sectional view, respectively, of a chemical concentrator according to a preferred embodiment of the present invention and designated generally by reference numeral 10. Concentrator 10 is shown attached to a syringe 100 having a needle 110 with a flat end 112. Syringe 100 is vertically supported above a thin layer chromatographic plate 120 by a syringe vise 130.

Concentrator 10 has a T-shape with a first annular branch 20, a second annular branch 30, and a third annular branch 40. First branch 20 and second branch 30 are in axial alignment, while third branch 40 is perpendicular to first and second branches 20 and 30. Third branch 40 is in fluid communication with a source of gas 50 via conduit 56. Concentrator 10 as well as conduit 56 may be made of any material commonly used in the art. As can be seen most clearly in FIG. 3, first branch 20 is formed with an inner diameter 22 which frictionally engages outer diameter 114 of needle 110 to provide a fluid-tight seal therebetween. Moreover, inner diameter 22 ensures that needle 110 is properly centered within concentrator 10. Preferably, inner diameter 34 of second branch 30 is approximately 3.5 mm. Concentrator 10 and conduit 56 can be made of any polymeric material commonly employed in the art. Preferably, concentrator 10 is made of a plastic compound sold under the trademark NALGENE, while conduit 56 is made using vinyl compounds sold under the trademark TYGON.

Gas source 50 can be any gas commonly employed in the art of analytical chemistry capable of providing a gas flow rate of between approximately 500 and 1500 ml/min. Gases which can be used with the present invention include, but are not limited to, nitrogen and an inert gas such as helium, neon, or argon. Positioned between gas source 50 and chemical concentrator 10 is a heat source 60. Heat source 60 serves to increase the temperature of the gas prior to its introduction into concentrator 10. Heat source 60 may be any device commonly employed in the chemical arts which is capable of raising the gas temperature to between approximately 40° C. and 60° C. Preferably, heat source 60 is a hot water bath apparatus. Below plate 120 there is provided an optional hot plate 124 to heat the sample introduced to plate 120.

In use, syringe 100 is filled with the appropriate quantity of a sample and solvent mixture. Thereafter, concentrator 10 is placed over needle 110 by inserting end 112 into first branch 20 and applying a modest force, causing end 112 of needle 110 to extend beyond end 32 of second branch 30. Preferably, the distance between end 112 of needle 110 and end 32 of second branch 30 is approximately 3.0 millimeters.

Syringe vise 130 is then lowered until end 112 of needle 110 comes into contact with plate 120. Gas source 50 is then activated. Syringe vise 130, which can be either manually or electronically controlled, is then activated to inject sample and solvent mixture into plate 120. The rate of injection of the sample and solvent mixture will vary in accordance with the solvent being used. Normally, for a 100 µL solution, it requires between 5 and 10 minutes to fully inject the mixture.

Gas from gas source 50, traveling at a flow rate of between approximately 500 and 1500 ml/min, will enter heat source 60 and increase in temperature to between approximately 40° C. and 60° C. The gas will then travel into concentrator 10 via third branch 40 and be expelled from second branch 30 in an annular pattern about plate 120. The annular flow of gas about plate 120 will evaporate the solvent and confine the sample to a geometrical area approximately equal to the outer diameter 114 of needle 110.

When the mixture is completely injected into plate 120, gas source 50 is deactivated.

Turning now to FIG. 2, concentrator 10 is shown attached to a horizontally positioned syringe 140 having a needle 146. Preferably, needle 146 is formed with a beveled end 148. Syringe 140 is preferably supported by a syringe vise 152.

In operation, concentrator 10 is positioned on syringe 140 with beveled end 148 extending a preselected distance beyond end 32. Gas source 50 is activated, forwarding gas through concentrator 10 and toward beveled end 148 in an annular pattern. Once gas flow about beveled end 148 has been established, syringe vise 152 is activated, causing the sample and solvent mixture contained within syringe 140 to be urged toward beveled end 148. As the mixture is forwarded toward beveled end 148, the gas flow will cause the evaporation of the solvent and the precipitation of the sample at beveled end 148. The rate at which the mixture is forwarded toward beveled end 148 is a function of the solvent. Normally, a 100 µL solution takes approximately 15 minutes to be effectively forwarded to beveled end 148.

When there remains approximately 2 µL within syringe 140, syringe vise 152 is deactivated and the flow of gas is discontinued. At this point there exists at beveled end 148 a concentrated sample. For example, a 100 µL solution, once concentrated at beveled end 148, will contain approximately 98% analyte at end 148 of needle 146 with at least 2% analyte remaining in solution. Syringe 140 is then removed from vice 152. Plunger 149 of syringe 140 is then pulled back, and the analyte residing at beveled end 148 and the 2 µL mixture within syringe 140 is injected into the appropriate gas chromatograph or high pressure liquid gas chromatograph. Since 100% analyte is introduced into the chromatograph, an increase of 50 in sensitivity can be obtained if compared to prior art chromatographic techniques (2 µL injection of 100 µL solution).

When using the analytical technique of capillary electrophoresis, the sample is concentrated at beveled end 148 in the same manner as detailed above. Syringe 140 is then removed from vice 152. Thereafter, the concentrated sample is introduced to the capillary electrophoresis instrument using techniques commonly employed in the art of analytical chemistry.

Figure 4A:
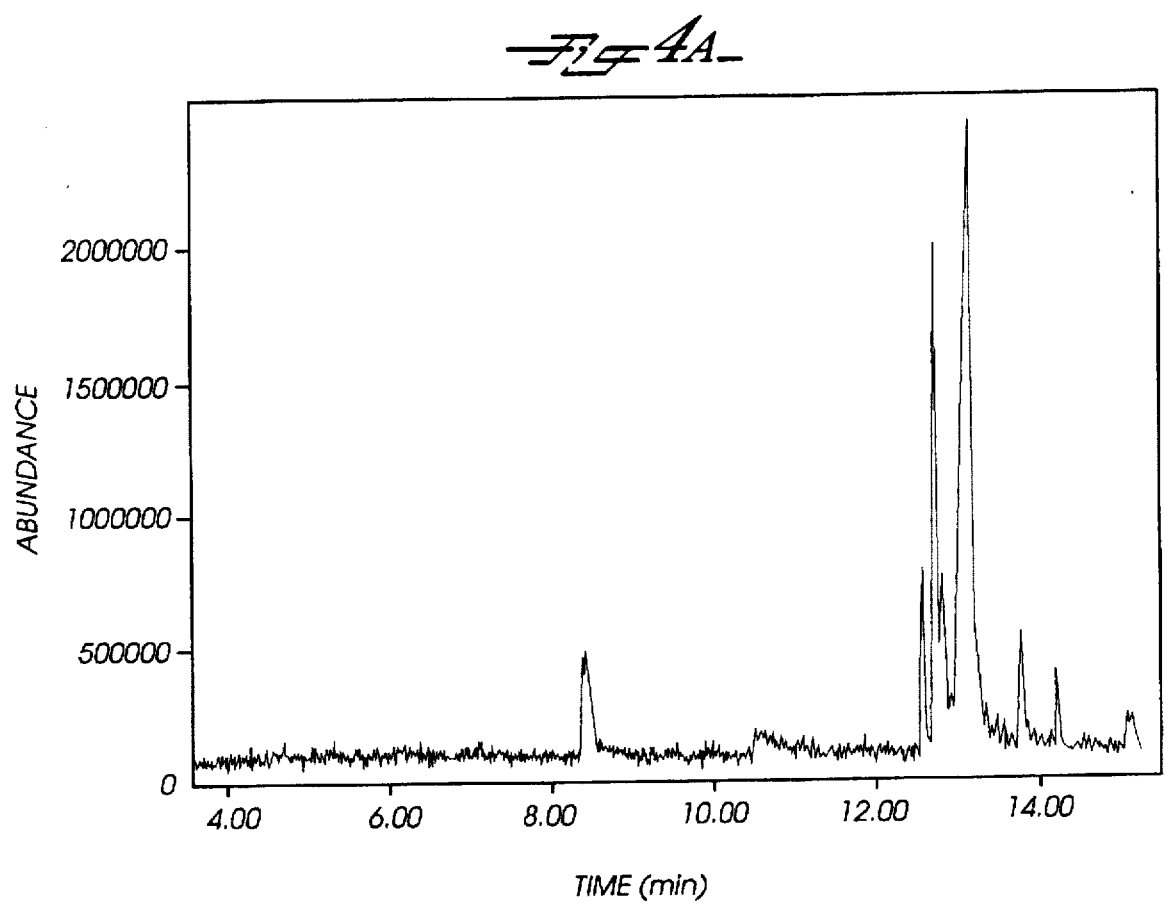
FIG. 4a is a gas chromatogram obtained from a sample known to contain a mixture of antidepressants using prior art chromatographic techniques.
Figure 4B:
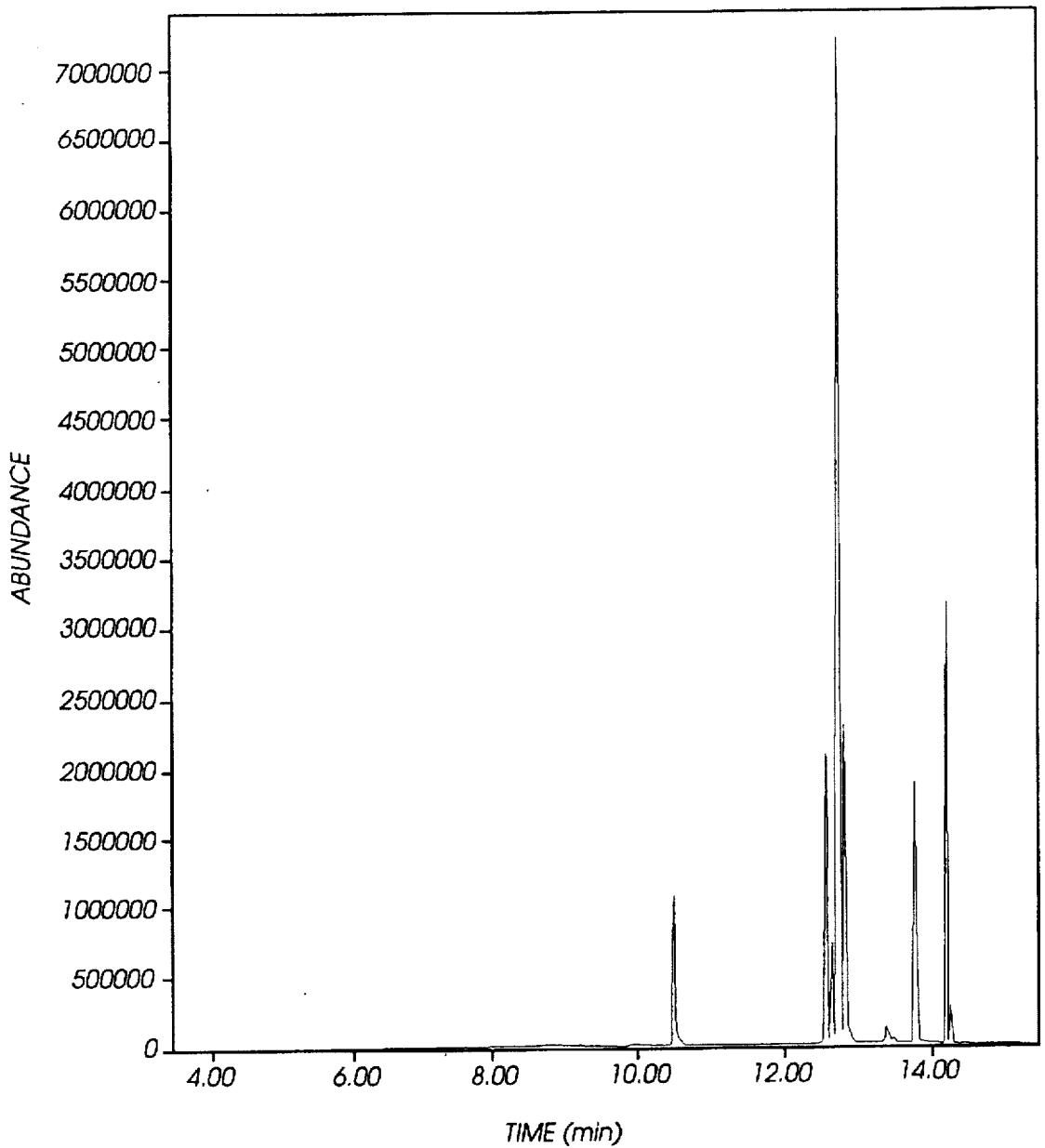
FIG. 4b is a gas chromatogram obtained from the same sample of FIG. 4a, using a chemical concentrator, using a method according to a preferred embodiment of the present invention.
Figure 5A:
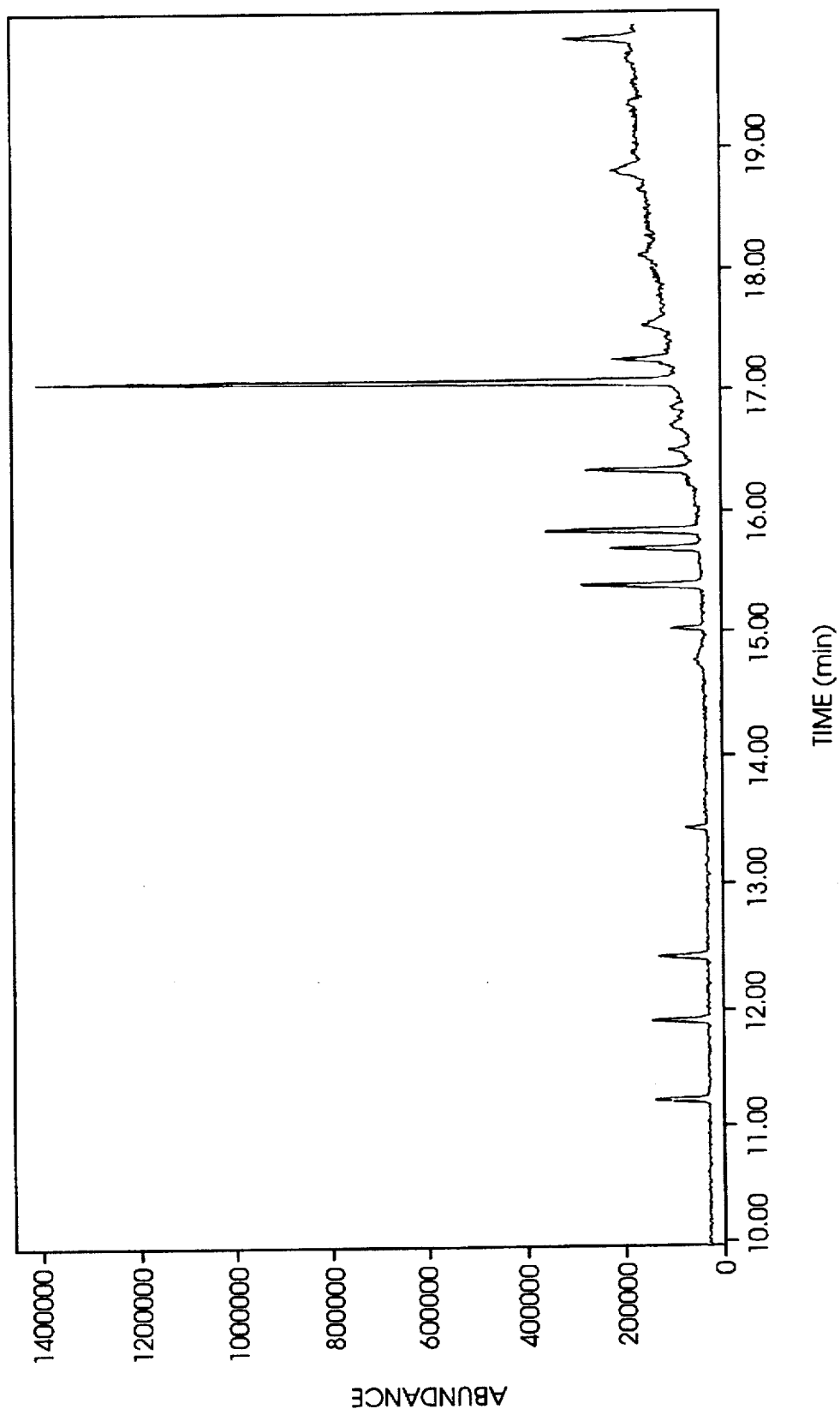
FIG. 5a is a gas chromatogram obtained from a sample known to contain environmentally deleterious pesticides using prior art chromatographic techniques.
Figure 5B:
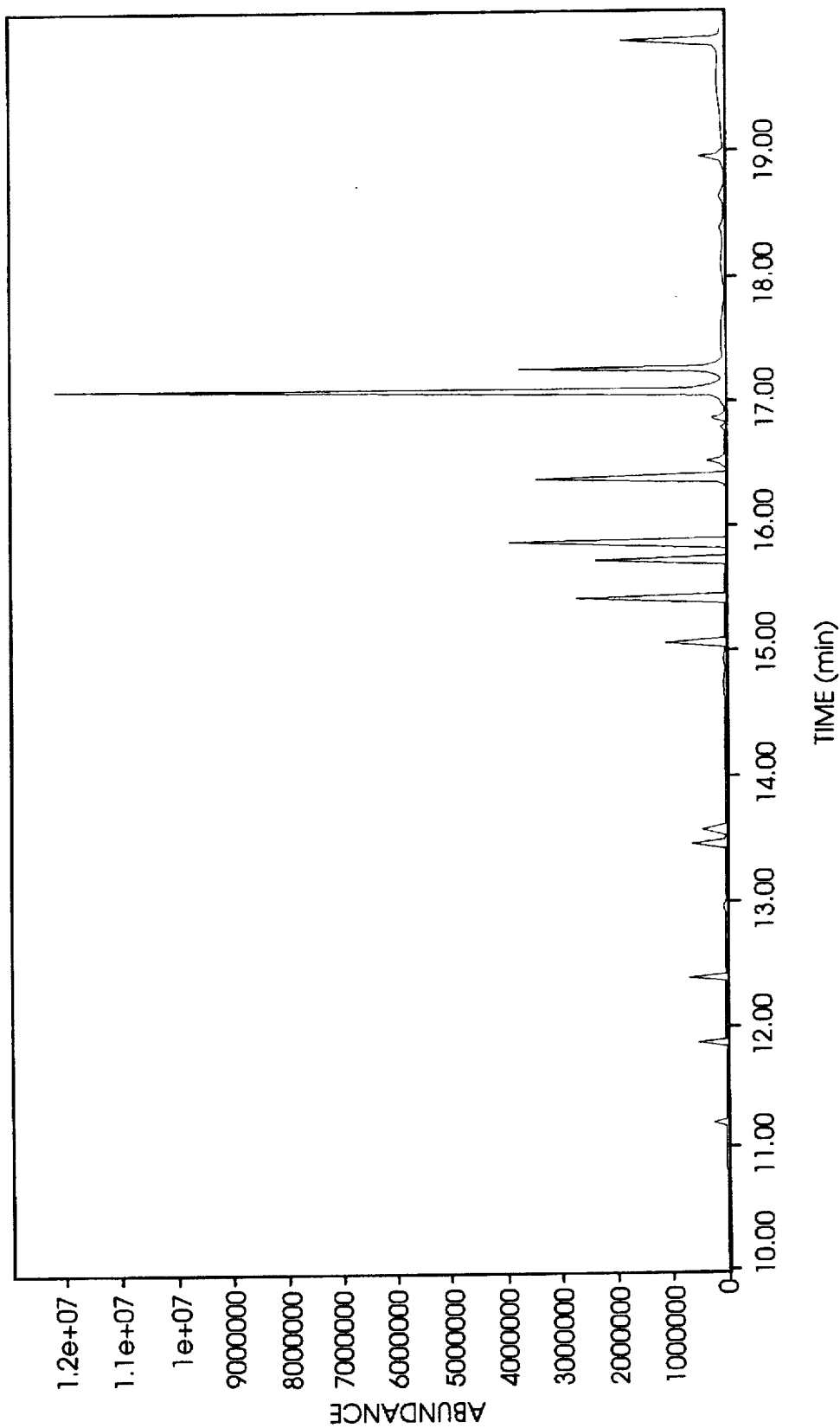
FIG. 5b is a gas chromatogram obtained from the same sample of FIG. 5a, using a chemical concentrator, using a method according to a preferred embodiment of the present invention.

Turning now to FIGS. 4a and 4b, there is shown a gas chromatogram on a sample known to contain a mixture of antidepressants using the prior art method and a comparative chromatogram on the same sample that was prepared using concentrator 10 and the present method. As will be apparent to those with ordinary skill in the art of analytical chemistry, the use of concentrator 10 provides significantly increased sensitivity, which in turn increases the accuracy of the chemical profile. The same increase in sensitivity can be seen in FIGS. 5a and 5b. FIGS. 5a and 5b show the gas chromatographic analysis, again using prior art techniques, of a sample known to contain environmentally deleterious pesticides, with FIG. 5b representing the same sample having been prepared using concentrator 10 and the present method.

It will be clear to those skilled in the art of analytical chemistry that many modifications and substitutions can be made without departing from the spirit and scope of the invention, which is defined by the appended claims.

What is claimed is:

1. A chemical concentrator for use with a plate, said concentrator comprising:

a frame adapted for carrying a plate;

a syringe having a needle, said needle having an outer diameter and an end;

means for holding said end of said syringe in contact with said plate, said needle adapted for depositing a chemical from said syringe onto an area of said plate, said area defined by said needle, when said needle is held in contact with said plate by said holding means and said plate is carried by said frame;

a first annular branch having an inner diameter, said inner diameter of said first branch frictionally engaging the outer diameter of said needle;

a second annular branch in fluid communication with said first branch, said second annular branch being in axial alignment with said first branch, said second branch having an end and an inner diameter, wherein said end of said needle extends a preselected distance beyond said end of said second branch;

a third annular branch in fluid communication with said first and said second branch, said third branch being perpendicular to said first and said second branch; and a gas source in fluid communication with said third branch, said gas source providing gas at a preselected flow rate to said third branch so that said gas enters said third branch and is expelled from said second branch in an annular pattern, said gas confining and drying said chemical from said needle to said area.

2. The chemical concentrator as recited in claim 1, further comprising a heat source in operational connection with said gas source, said heat source heating said gas to a temperature between approximately 40° C. and 60° C.

3. The chemical concentrator as recited in claim 1, wherein said preselected flow rate is between approximately 500 and 1500 ml/min.

4. The chemical concentrator as recited in claim 1, wherein said preselected distance is approximately 3.0 mm.

5. The chemical concentrator as recited in claim 1, wherein said gas is selected from the group consisting of nitrogen and an inert gas.

6. The chemical concentrator as recited in claim 1, wherein said inner diameter of said second branch is approximately 3.5 mm.

7. The chemical concentrator as recited in claim 1, wherein said chemical concentrator is made of a plastic compound.

8. A chemical concentrator for use with a plate, said concentrator comprising:

a frame adapted for carrying a plate;

a syringe having a needle, said needle having an outer diameter and an end;

means for holding said end of said syringe in contact with said plate, said needle adapted for depositing a chemical from said syringe onto an area of said plate, said area defined by said needle, when said needle is held in contact with said plate by said holding means and said plate is carried by said frame;

a first annular branch having an inner diameter, said inner diameter of said first branch frictionally engaging the outer diameter of the needle;

a second annular branch in fluid communication with said first branch, said second annular branch being in axial alignment with said first branch, said second branch having an end and an inner diameter, wherein the end of the needle extends a preselected distance beyond said end of said second branch;

a third annular branch in fluid communication with said first and said second branch, said third branch being perpendicular to said first and said second branch;

a gas source in fluid communication with said third branch, said gas source providing gas at a flow rate between approximately 500 and 1500 ml/min to said chemical concentrator so that said gas enters said third branch and is expelled from said second branch in an annular pattern; and a heat source in operational connection with said gas source, said heat source heating said gas to preselected temperature, said gas confining and drying said chemical from said needle to said area.

9. The chemical concentrator as recited in claim 8, wherein said preselected temperature is between approximately 40° C. and 60° C.

10. The chemical concentrator as recited in claim 8, wherein said preselected distance is approximately 3.0 mm.

11. The chemical concentrator as recited in claim 8, wherein said gas is selected from the group consisting of nitrogen and an inert gas.

12. The chemical concentrator as recited in claim 8, wherein said inner diameter of said second branch is approximately 3.5 mm.

13. The chemical concentrator as recited in claim 8, wherein said chemical concentrator is made of a plastic compound.

* * * * *